United States Patent [19]

Howarth

[11] 4,129,099
[45] Dec. 12, 1978

[54] GALVANIC EXHAUST GAS SENSOR WITH SOLID ELECTROLYTE

[75] Inventor: David S. Howarth, Rochester, Mich.

[73] Assignee: General Motors Corporation, Detroit, Mich.

[21] Appl. No.: 787,900

[22] Filed: Apr. 15, 1977

[51] Int. Cl.² .......................................... G01N 27/46
[52] U.S. Cl. ........................ 123/32 EE; 123/119 EC; 204/15; 204/195 S; 60/276; 429/33
[58] Field of Search .......... 123/32 EE, 32 EJ, 254 E, 123/119 E; 73/27 R, 26; 204/15, 195 S; 60/276; 429/33

[56] References Cited

U.S. PATENT DOCUMENTS

| | | | |
|---|---|---|---|
| 3,616,274 | 10/1971 | Eddy | 123/119 E |
| 3,773,641 | 11/1973 | Fitterer | 204/195 S |
| 3,847,778 | 11/1974 | Riddel | 123/119 E |
| 3,935,089 | 1/1976 | Jogawa et al. | 204/195 S |
| 3,960,693 | 6/1976 | Weyl et al. | 123/119 E |
| 4,034,730 | 7/1977 | Ayres et al. | 123/119 E |
| 4,061,117 | 12/1977 | Ikeura | 123/32 EE |

Primary Examiner—Charles J. Myhre
Assistant Examiner—R. A. Nelli
Attorney, Agent, or Firm—Robert J. Wallace

[57] ABSTRACT

Apparatus and method for controlling internal combustion engine air to fuel ratios that includes a solid oxide electrolyte galvanic-type exhaust gas sensor. The sensor electrolyte is doped to have a significant internal thermally varying electronic conductivity, that materially reduces variation in sensor output voltage with variations in temperature. A dopant such as iron oxide provides substantially complete temperature compensation of the output voltage at sensor operating temperatures above about 450° C.

7 Claims, 5 Drawing Figures

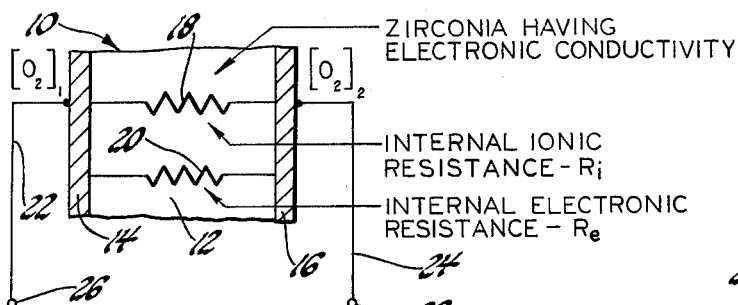
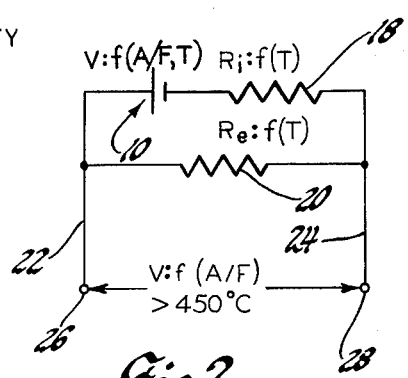
Fig.1  Fig.2
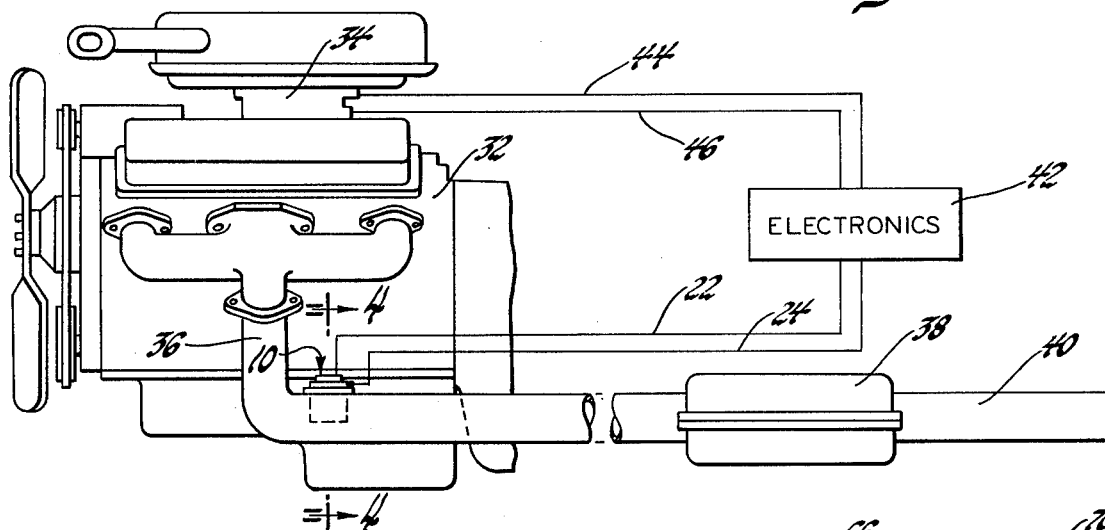
Fig.3
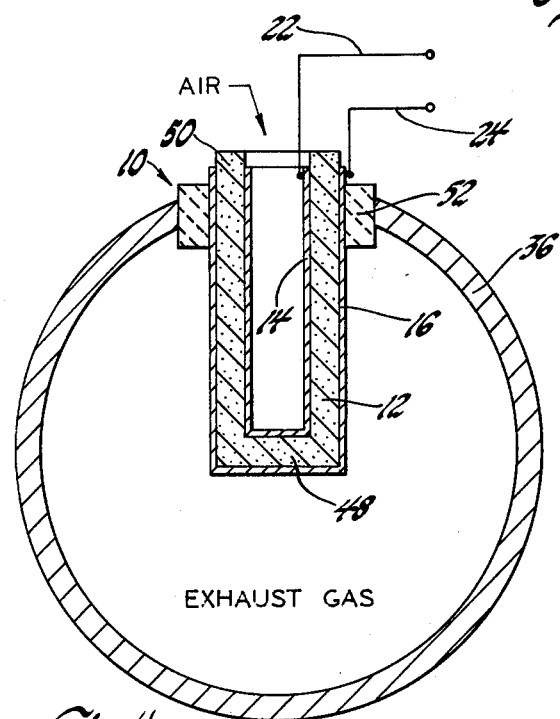
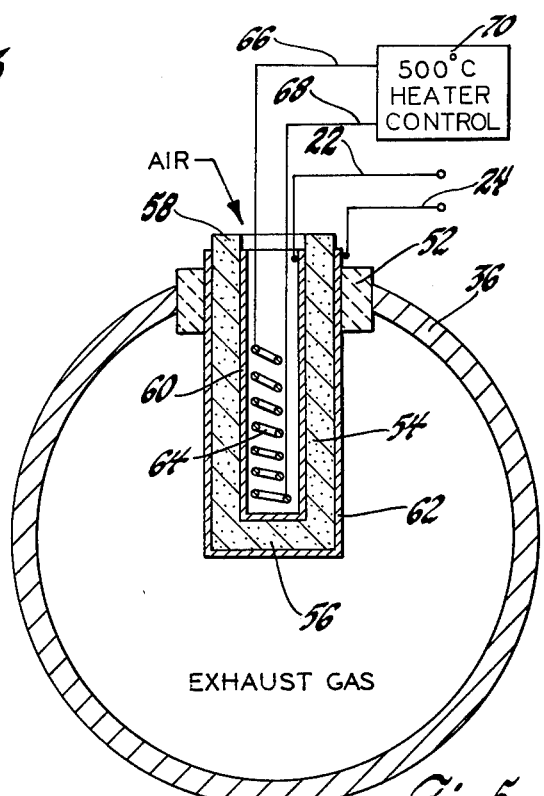
Fig.4  Fig.5

GALVANIC EXHAUST GAS SENSOR WITH SOLID ELECTROLYTE

BACKGROUND OF THE INVENTION

This invention relates to galvanic sensors, and more particularly to solid oxide electrolyte galvanic sensors for exhaust gases.

A solid electrolyte galvanic sensor can be used to measure the chemical content of combustion gases produced in an internal combustion engine. The sensor produces an output voltage that can be used as a direct measure of oxygen or unburned combustibles in the combustion gases. It can be used in monitoring and controlling the combustion process. U.S. Pat. Nos. 3,616,274, Eddy and 3,844,920, Burgett et al. disclose sensors of this type.

The sensor can be a tube of oxygen-ion-conductive ceramic, such as zirconia, having inner and outer electrodes. The inner electrode is exposed to a reference gas of known oxygen partial pressure, as for example air. The outer electrode is exposed to the combustion gases. If the combustion gases are from a fuel-lean air-fuel mixture, the sensor has a low output voltage. If the combustion gases are from a fuel-rich air-fuel mixture, the sensor has a high output voltage. The change from low to high output occurs within a narrow range of air-fuel mixtures that are substantially stoichiometric in composition. Sensor output voltage can thus be used to detect whether a lean, rich or stoichiometric air-fuel mixture was combusted.

Sensor output voltage also varies with temperature, particularly when analyzing exhaust gases from fuel-lean air-fuel mixtures. At a fixed exhaust gas composition and below about 800° C., sensor output voltage generally decreases with increasing temperature. Above about 800° C., output voltage no longer decreases. It becomes relatively constant and in fact increases slightly. However, for purposes of this invention, sensor output voltage is considered to be substantially independent of temperature above about 800° C. The aforementioned U.S. Pat. No. 3,616,274 Eddy avoids temperature effects by maintaining the sensor at a constant operating temperature. I have recognized that a temperature dependent resistance, connected across the sensor output, can be used to compensate for temperature effects. Moreover, I have found how to provide such a resistance in a simple and effective manner. The solid electrolyte of my sensor is doped to have a predetermined thermally dependent electronic conductivity. The electronic conductivity provides an internal electronic resistance that is electrically in shunt across the sensor output. The electronic resistance decreases with increasing temperatures. Such doping can provide a sensor output voltage that is substantially independent of temperature above temperatures as low as about 450° C.

OBJECTS AND SUMMARY OF THE INVENTION

An object of this invention is to provide an internal combustion engine assembly having an improved solid electrolyte exhaust gas sensor.

A further object is to provide improved apparatus for maintaining preselected air to fuel ratios of air-fuel mixtures combusted in an internal combustion engine.

Still further objects of the invention are to provide improved methods of internal combustion engine exhaust gas analysis and of regulating air-fuel mixtures combusted in internal combustion engines.

This invention involves an internal combustion engine with a galvanic-type solid electrolyte exhaust gas sensor. The sensor electrolyte includes a dopant that produces a significant electronic conductivity therein. The electronic conductivity acts as an internal temperature dependent shunt across the sensor electrodes. It confines decreases in sensor output voltage with increasing temperature to lower temperatures. Above these temperatues, sensor output voltage is substantially independent of temperature. Dopant concentrations of about 4 mole percent in the electrolyte crystal matrix provide a sensor output voltage for fuel lean air-fuel mixtures that is substantially independent of temperature above about 450° C.

BRIEF DESCRIPTION OF THE DRAWINGS

Other objects, features and advantages of the invention will become more apparent from the following description of preferred examples thereof and from the drawings, in which:

FIG. 1 shows a diagrammatic view of a zirconia galvanic sensor made in accordance with the invention;

FIG. 2 shows a circuit diagram of the sensor illustrated in FIG. 1;

FIG. 3 diagrammatically shows an elevational side view of an internal combustion engine and its exhaust system;

FIG. 4 shows an enlarged fragmentary sectional view along the line 4—4 of FIG. 3; and FIG. 5 shows an alternate embodiment of the invention illustrated in FIG. 4.

DESCRIPTION OF THE PREFERRED EMBODIMENTS

FIG. 1 shows a solid electrolyte exhaust gas sensor 10 of the galvanic type made in accordance with this invention. Sensor 10 has a stabilized zirconia electrolyte body 12 with platinum electrodes 14 and 16 on opposed faces of the body. The zirconia of body 12 is doped with about 8 mole percent yttria or 15 mole percent calcia to stabilize it in its cubic crystalline phase. This phase is conductive to oxygen ions and has a fluorite-like lattice structure referred to herein as the electrolyte crystal matrix. Ionic conductivity of electrolyte body 12 can be considered as an internal resistance $R_i$ (indicated by reference numeral 18). Ionic conductivity increases with increasing temperature. Under substantially open circuit conditions, decreasing ionic resistance in prior sensors has a negligible effect. In prior sensors, electrode effects and the like predominated, and sensor output voltage decreased with increasing temperature to about 800° C. These other effects can be considered as providing an output voltage, apart from ionic resistance, that decreases with increasing temperature. Output voltage, of course, also varies with exhaust gas composition, which is a function of air-to-fuel ratio. It is, therefore, considered to be a voltage $V:f(A/F, T)$ that is a function of air-to-fuel ratio (A/F) and temperature (T).

Zirconia body 12 is also doped with at least about 5 mole percent iron oxide, with about 80% of it substitutionally in the electrolyte crystal matrix. This imparts an electronic conductivity to zirconia body 12, in addition to the ionic conductivity normally present. The electronic conductivity increases with increasing temperature. It can be considered as a separate internal resistance $R_e$ (indicated by reference numeral 20) that decreases with increasing temperature. Electrodes 14 and 16 have leads 22 and 24 extending therefrom to terminals 26 and 28, respectively. Open circuit output voltage across terminals 26 and 28 is substantially independent of temperature from 450° C. to about 900° C.

FIG. 2 shows the internal resistances 18 and 20 of FIG. 1 as equivalent external resistances, so that their effects can be more clearly understood. In FIG. 2, sensor 10 is shown as having a temperature dependent output voltage apart from resistances 18 and 20, as is attributable to electrode effects and the like. Ionic resistance ($R_i$) 18 is shown in series with the galvanic voltage $V:f(A/F,T)$ since it internally has this effect. Electronic resistance ($R_e$) 20 is analogously shown in shunt across sensor leads 22 and 24, since it internally is an electrical shunt between electrodes 14 and 16. Hence, it can then be seen that electronic resistance $R_e$ is not in series but in parallel with ionic resistance $R_i$ and cell output voltage $V:f(A/F,T)$ and forms part of voltage divider $R_i - R_e \cdot R_i$ decreases more rapidly with increasing temperature than does $R_e$. At lower temperatures, $R_e$ produces an initial voltage drop with increasing temperature. However, with further increases in temperature $R_i$ decreases more rapidly and, at a fixed A/F, output voltage across terminals 26 and 28 is stabilized.

As previously mentioned, temperature stability of the sensor is most important when it is used to detect combustion products from fuel-lean air-fuel mixtures. FIG. 3 shows the sensor 10 of FIGS. 1 and 2 in a closed loop fuel control system for an internal combustion engine that burns fuel-lean air-fuel mixtures. FIG. 3 shows an internal combustion engine 32 having an air-fuel mixture control means 34 and an exhaust pipe 36. Control means 34 is designed to adjust the ratio of air-to-fuel entering engine 32 for combustion to a ratio greater than about the stoichiometric ratio, and engine 32 is designed to operate on such mixtures. Sensor 10 is mounted within exhaust pipe 36 upstream from a catalytic converter 38. Exhaust gases emitted from the engine 32 pass through exhaust pipe 36 where sensor 10 is exposed to them. The exhaust gases are then passed through catalytic converter 38 into a tailpipe 40. Leads 22 and 24 from sensor 10 extend to an electronic control unit 42. Electronic control unit 42 is responsive to the output voltage of sensor 10 and generates a control signal to be sent via leads 44 and 46 to the air-fuel mixture control means 34. The air-fuel mixture control means 34 responds to the control signal of electronic control unit 42, and regulates the ratio of air to fuel introduced into engine 32 as it is directed.

Sensor 10 is preferably located sufficiently close to the inlet of exhaust pipe 36 that the engine exhaust gases will heat sensor 10 to a temperature above about 450° C. In such instance, means for heating sensor 10 above 450° C. is inherently provided.

FIG. 4 shows an enlarged sectional view of sensor 10 as it is mounted in exhaust pipe 36. Electrolyte body 12 is a cylindrical tube, one end 48 of which is closed and exposed to exhaust gases within exhaust pipe 36. The opposite end 50 of tube 12 is open and exposed to ambient air. The inner surface of tube 12 is coated with a platinum electrode 14. Electrode 14 is exposed to air entering tube 12 through its open end 50. The outer surface of tube 12 is also coated with a platinum electrode 16 for interaction with the exhaust gas. Sensor 10 is supported within the exhaust pipe 36 by means of a sealing member 52.

The zirconia of body 12 is preferably stabilized in its ion conductive cubic crystal form with yttria or calica. However, it is also known that additions of rare earth oxides will also produce such stabilization. It is expected that they would be equally useful in this invention also. It is also expected that body 12 could be of any oxygen ion conductive oxide or solid solution of oxides of the fluorite-type crystal structure. This suggests that the invention may also be useful with solid solutions of oxides having the perovskite crystal structure. This invention does not preclude a decline in sensor output voltage as temperature increases. However, it confines the decline to a low operating temperature range. Above that temperature range, sensor output voltage is substantially thermally stable. It is known that prior sensors are substantially temperature stable above 800° C. Tests of my sensor at temperatures up to above 600° C. indicate that such temperature stability is now achievable at lower temperatures. For example, with 3.4 mole percent iron oxide in the electrolyte-crystal matrix, sensor output voltage across leads 22 and 24 is substantially thermally stable above 570° C. With 3.8 mole percent in the electrolyte crystal matrix, it is substantially thermally stable above 500° C. With 4.0 mole percent in the electrolyte crystal matrix it is substantially thermally stable above 450° C. It is believed that higher electrolyte crystal matrix concentrations would provide a thermal stability that begins at even lower temperatures. Five mole percent iron oxide in the electrolyte crystal matrix may provide temperature stability as low as 350° C. If so, the device would be temperature stable over the full operating range of about 350° C. to 900° C. that is desired for detecting internal combustion engine exhaust gases. By electrolyte crystal matrix concentration I refer to the concentration of iron and oxygen atoms in substitutional positions of the solid electrolyte lattice, and do not include segregated iron oxide in or around individual solid electrolyte crystals.

Using conventional techniques used to make stabilized zirconia electrolyte bodies, it appears that at least half of the cations of the doping oxide will enter the electrolyte crystal matrix. The balance will be segregated in and around electrolyte crystals. On this assumption, if 4.0 mole percent iron oxide is desired in the electrolyte crystal matrix, about 8 mole percent total iron oxide should be included in the oxide mixture from which the electrolyte body is made. With finer milling, more homogeneous mixtures and sintering temperatures of about 1400° C. to 1600° C., about 60-80% of the cations appear to enter the electrolyte crystal matrix, permitting a correspondingly lesser total concentration of iron oxide to be used. In general, a total iron oxide concentration of about 4-8 mole percent can be used to produce the electrolyte crystal matrix concentrations mentioned. For simplicity, iron oxide, manganese oxide and cerium oxide content is calculated as $Fe_2O_3$, $Mn_3O_4$ and $CeO_2$, respectively, regardless as to the complex oxides that may be formed in the finished product.

Iron oxide has been found to be effective as an electronic conductivity inducing dopant. However, it appears that manganese oxide and cerium oxide would also be effective, in about the same molar concentrations as iron oxide. $Mn_3O_4$ and $CeO_2$ can be used. In addition, any oxide or thermally decomposable salt of iron, manganese or cerium appears useful in this invention, since electrolyte body 12 is prepared by calcining and sintering in air. For example, more homogeneous mixtures of iron oxide in the other oxides can be obtained by dissolving ferric nitrate in water, blending it with the oxide mixture, and thermally decomposing it to iron oxide during calcining. It is believed that equivalent amounts of such other oxides and salts of the named oxide will produce substantially the same resultant composition in the finished product.

In describing FIG. 4 it was mentioned that sensor 10 is preferably positioned close enough to the inlet of exhaust pipe 36 that sensor 10 will be inherently heated to a temperature above 450° C. If this is impractical, or if supplementary heating is desired for faster sensor warmup, the sensor can be heated by other means. For example, the resistance heating means shown in FIG. 5 can be used. Aside from the resistance heating means, the sensor of FIG. 5 is identical to that illustrated in FIG. 4. It includes a yttria stabilized zirconia tube 54 containing 4 mole percent iron oxide in the electrolyte crystal matrix. Tube 54 is closed at its lower end at 56. It is open at its upper end 58 so that its inner platinum electrode 60 is exposed to ambient air. Tube 54 also has an outer platinum electrode 62 for contact with exhaust gas in exhaust pipe 36. A resistance heater 64 is disposed within tube 54 and connected by leads 66 and 68 to a heater control unit 70. Heater control unit 70 maintains the temperature of tube 54 at a temperature greater than about 500° C. Precise temperature control is unnecessary. Thus, the sensor can be positioned in exhaust pipe 36 further downstream from engine 32. However, it would still be upstream from catalytic converter 38. If resistance heater 64 is used merely for more rapid warmup, heater control unit 70 would turn heater 64 off after the sensor has reached its operating temperature as heated by the exhaust gases.

It should also be noted that the control signal from sensors of this type is usually a substantially open circuit output potential, indicating the composition of the exhaust gases. By open circuit, I mean a load is placed across terminals 26 and 28 that has a resistance at least several orders of magnitude greater than cell internal resistances. However, it should also be recognized that temperature compensation effects of this invention are also observed in the cell closed circuit output potential. It is generally preferred to use open circuit potentials to obtain maximum device sensitivity. However, it should be recognized that it may be desirable to reduce the usual impedance of the load slightly, and trim the load of individual sensors to obtain a plurality of sensors all having precisely the same output voltage characteristics. If the resistance of the load in this latter instance is still more than several orders of magnitude greater than cell internal resistance, it should still be construed as providing a substantially open circuit output potential.

I claim:

1. An internal combustion engine assembly comprising a spark ignition internal combustion engine, means defining an exhaust passage for directing exhaust gases emitted from said engine, a galvanic-type sensor exposed to said exhaust gases in said passage and responsive to exhaust gas constituents at various temperatures up to 900° C., said sensor having as an active element an oxygen ion conductive solid oxide electrolyte effective to produce an output voltage that is representative of exhaust gas chemical contact, said electrolyte having a fluorite-type crystal matrix doped with at least one electronic conductivity-inducing dopant selected from the group consisting of iron oxide, manganese oxide and cerium oxide that provides a temperature dependent electronic conductivity therein, said dopant induced electronic conductivity in sense and amount to provide a sensor output voltage substantially independent of temperature above a preselected temperature less than about 600° C., heating means for maintaining said sensor between said preselected temperature and 900° C. whereby sensor output voltage is substantially temperature independent, and means having a high internal electronic resistance responsive to the output voltage of said sensor.

2. Apparatus for maintaining preselected air to fuel ratios of air-fuel mixtures combusted in an internal combustion engine, said apparatus comprising means responsive to an electronic control signal for regulating the ratio of air to fuel of a mixture introduced into an internal combustion engine, a galvanic exhaust gas sensor contacting exhaust gases from air-fuel mixtures combusted in said engine, said sensor having an oxygen ion conductive solid oxide electrolyte effective to produce an output voltage that is representative of exhaust gas chemical content, said electrolyte having a fluorite-type crystal matrix doped with at least one electronic conductivity-inducing dopant selected from the group consisting of iron oxide, manganese oxide and cerium oxide that provides a temperature dependent electronic conductivity therein, said dopant-induced electronic conductivity being in sense and amount to provide a sensor output voltage substantially independent of temperature above a preselected temperature below about 800° C., heating means for maintaining said sensor at a temperature within a range between said preselected temperature and 900° C. and producing a temperature independent sensor output voltage, and means responsive to said sensor output voltage for generating an air-fuel regulating means electronic control signal, which signal is representative of a preselected air-fuel mixture ratio.

3. Apparatus for maintaining preselected air to fuel ratios of air-fuel mixtures combusted in an internal combustion engine, said apparatus comprising means responsive to an electronic control signal for regulating the ratio of air to fuel of a fuel-lean mixture introduced into an internal combustion engine designed to burn such mixtures, a galvanic exhaust gas sensor contacting exhaust gases from such mixtures combusted in said engine, said sensor having a stabilized zirconia solid electrolyte effective to produce an output voltage representative of exhaust gas chemical content, about 4 to 8 mole percent of at least one electronic conductivity-inducing dopant selected from the group consisting of iron oxide, manganese oxide and cerium oxide, respectively calculated as $Fe_2O_3$, $Mn_3O_4$, and $CeO_2$, in said sensor solid electrolyte that induces a thermally dependent electronic conductivity in said electrolyte by which open circuit sensor output voltage is substantially independent of sensor temperature from about 450° C. to 900° C., heating means for maintaining said sensor within said range and producing a temperature independent sensor output voltage, and means responsive to said sensor output voltage for generating an air-fuel regulating means control signal which signal is representative of a preselected fuel-lean air-fuel mixture.

4. A process for regulating air-fuel mixtures combusted in an internal combustion engine comprising the steps of introducing an air-fuel mixture into an internal combustion engine for combustion therein, said combustion forming exhaust gases, exposing one electrode of a galvanic exhaust sensor to said exhaust gases while concurrently exposing a second electrode of said sensor to a reference atmosphere, said sensor having an oxygen ion conductive solid oxide electrolyte effective to produce a voltage in accordance with the concentration of said gaseous constituents and having a generally decreasing open circuit voltage output with increasing temperature, said solid oxide electrolyte having a fluorite-like crystal matrix doped with at least one electronic conductivity-inducing dopant selected from the group consisting of iron oxide, manganese oxide and cerium oxide, which dopant provides a temperature dependent electronic conductivity therein by which sensor output voltage is substantially independent of temperature at temperatures above a preselected temperature below about 800° C., maintaining said sensor electrolyte at a temperature within a range between said preselected temperature and 900° C. while respectively exposing said electrodes to said exhaust gases and said reference atmosphere to produce a sensor output voltage substantially independent of temperature, generating a control signal for regulating the ratio of air to fuel introduced into said engine in response to said sensor output voltage, and regulating the ratio of air to fuel introduced into said engine in response to said control signal.

5. A process for regulating fuel lean air-fuel mixtures combusted in an internal combustion engine comprising the steps of introducing a fuel lean air-fuel mixture into an internal combustion engine for combustion therein, said combustion forming exhaust gases, exposing one electrode of a galvanic exhaust sensor to said exhaust gases while concurrently exposing a second electrode of said sensor to a reference atmosphere, said sensor having an oxygen ion conductive solid oxide electrolyte effective to produce a voltage in accordance with the concentration of said gaseous constituents and having a generally decreasing open circuit voltage output with increasing temperature, said solid oxide electrolyte having a fluorite-like crystal matrix containing at least about 3 mole percent of an electronic conductivity inducing dopant selected from the group consisting of iron oxide, manganese oxide and cerium oxide, respectively calculated as $Fe_2O_3$, $Mn_3O_4$, and $CeO_2$, which dopant provides a temperature dependent electronic conductivity therein by which sensor output voltage is substantially independent of temperature at temperatures as low as about 450° C., maintaining said sensor electrolyte at a temperature between about 450° C. to 900° C. while respectively exposing said electrodes to said exhaust gases and said refereence atmosphere to produce a sensor output voltage substantially independent of temperature, generating a control signal for regulating the ratio of air to fuel of a fuel lean air-fuel mixture introduced into said engine in response to said sensor output voltage, and regulating said ratio of air to fuel introduced into said engine in response to said control signal.

6. A process for regulating fuel lean air-fuel mixtures combusted in an internal combustion engine comprising the steps of introducing a fuel lean air-fuel mixture into an internal combustion engine for combustion therein, said combustion forming exhaust gases, exposing one electrode of a galvanic exhaust sensor to said exhaust gases while concurrently exposing a second electrode of said sensor to a reference atmosphere, said sensor having a stabilized zirconia solid electrolyte effective to produce a voltage in accordance with the concentration of said gaseous constituents and having a generally decreasing open circuit voltage output with increasing temperature, said stabilized zirconia electrolyte having a crystal matrix containing about 3-5 mole percent iron oxide, calculated as $Fe_2O_3$, which provides a temperature dependent electronic conductivity therein by which sensor open circuit output voltage is substantially independent of temperature at temperatures as low as about 450° C., maintaining said sensor electrolyte at a temperature between about 450° C. to 900° C. while respectively exposing said electrodes to said exhaust gases and said reference atmosphere to produce a sensor output voltage substantially independent of temperature, generating a control signal for regulating the ratio of air to fuel of a fuel lean air-fuel mixture introduced into said engine in response to said sensor output voltage, and regulating said ratio of air to fuel introduced into said engine in response to said control signal.

7. A method of analyzing the constituents of an internal combustion engine exhaust gas stream at varying temperatures, said method comprising combusting air-fuel mixtures in a spark ignition internal combustion engine to produce exhaust gases, directing a stream of said exhaust gases to a galvanic-type exhaust gas sensor, exposing said sensor to said stream for response to gaseous constituents therein at varying temperatures, said galvanic exhaust sensor having an oxygen ion conductive solid oxide electrolyte effective to produce an output voltage that is representative of exhaust gas chemical contact, said electrolyte having a fluorite-type crystal matrix doped with at least one conductivity-inducing dopant selected from the group consisting of iron oxide, manganese oxide and cerium oxide that provides a temperature independent electronic conductivity therein, said dopant induced electronic conductivity being in sense and amount to provide a sensor output voltage substantially independent of temperature above a preselected temperature below about 600° C., maintaining said sensor electrolyte at a temperature between said preselected temperature and 900° C. to produce a sensor output voltage substantially independent of temperature, and generating an indicating signal in response to said sensor output voltage.

* * * * *